United States Patent [19]

Cerami et al.

[11] Patent Number: 5,399,560
[45] Date of Patent: Mar. 21, 1995

[54] 1,2,4-TRIAZINE PRODUCTS RESULTING FROM THE INHIBITION OF ADVANCED GLYCOSYLATION

[75] Inventors: Anthony Cerami, Shelter Island; Hauh-Jyun C. Chen, White Plains, both of N.Y.

[73] Assignee: The Rockefeller University, New York, N.Y.

[21] Appl. No.: 956,722

[22] Filed: Oct. 1, 1992

Related U.S. Application Data

[60] Continuation-in-part of Ser. No. 805,200, Dec. 10, 1991, Pat. No. 5,238,963, and a continuation-in-part of Ser. No. 605,654, Oct. 30, 1990, Pat. No. 5,140,048, said Ser. No. 805,200, is a division of Ser. No. 481,869, Feb. 20, 1990, Pat. No. 5,128,360, which is a continuation-in-part of Ser. No. 220,504, Jul. 18, 1988, abandoned, which is a division of Ser. No. 798,032, Nov. 14, 1985, Pat. No. 4,758,583, which is a division of Ser. No. 590,820, Mar. 19, 1984, Pat. No. 4,665,192, said Ser. No. 605,654, is a continuation-in-part of Ser. No. 264,930, Nov. 2, 1988, Pat. No. 4,983,604, which is a continuation-in-part of Ser. No. 119,958, Nov. 13, 1987, Pat. No. 4,908,446, which is a continuation-in-part of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.[6] .................... A61K 31/53; C07D 253/065
[52] U.S. Cl. ..................... 514/242; 514/243; 544/182; 544/183; 544/184
[58] Field of Search ............... 514/242, 243; 544/182, 544/184, 183

[56] References Cited

U.S. PATENT DOCUMENTS

| | | | |
|---|---|---|---|
| 4,665,192 | 5/1987 | Cerami et al. | 548/336 |
| 4,758,583 | 7/1988 | Cerami et al. | 514/399 |
| 4,908,446 | 3/1990 | Ulrich et al. | 540/553 |
| 4,983,604 | 1/1991 | Ulrich et al. | 514/238.5 |
| 5,017,696 | 8/1991 | Farmar et al. | 536/18.7 |
| 5,128,360 | 7/1992 | Cerami et al. | 514/400 |
| 5,140,048 | 8/1992 | Ulrich et al. | 514/601 |

OTHER PUBLICATIONS

Huber et al. Carbohydrate Res., 204:215–220 (1990).
Hirsch et al., Carbohydrate Res. 220:C–5–C–7 (1991).

*Primary Examiner*—Mukund J. Shah
*Assistant Examiner*—Y. N. Gupta
*Attorney, Agent, or Firm*—Klauber & Jackson

[57] ABSTRACT

The mechanism of the inhibition of advanced glycosylation by aminoguanidine and other hydrazine type compounds was investigated using a solution of one or two molecules of aminoguanidine or other hydrazine type compound incubated with an Amadori product (1-propylamine-1-deoxy-D-fructose) under physiological conditions. This inhibition was found to proceed through the reactive intermediate 1-propylamino-1, 4-dideoxyosone to form the corresponding triazine and the dehydrazone of 1,4-dideoxyglucosone, respectively.

The triazine and dehydrazone products are useful as macrophage stimulants to activate a macrophage to effect removal of advanced glycosylation endproducts (AGEs). Additionally, they can be used in a variety of investigative methods in an effort to measure the extent of nonenzymatic glycosylation of a protein sample wherein aminoguanidine or other hydrazine-type compound is or was present during the glycosylation process.

7 Claims, No Drawings

1,2,4-TRIAZINE PRODUCTS RESULTING FROM THE INHIBITION OF ADVANCED GLYCOSYLATION

This invention was made in part with Government support under Grant No. DK-19655 awarded by the National Institutes of Health. The Government may have certain rights in this invention.

CROSS-REFERENCE TO RELATED APPLICATIONS

This is a continuation-in-part of application Serial No. 07/805,200, filed Dec. 10, 1991, now U.S. Pat. No. 5,238,963 and 07/605,654, filed Oct. 30, 1990, now U.S. Pat. No. 5,140,048; said Ser. No. 07/805,200, being a division of Ser. No. 481,869, filed Feb. 20, 1990, and now U.S. Pat. No. 5,128,360; which is a continuation-in-part of Ser. No. 220,504, filed Jul. 18, 1988, and now abandoned; which is a division of Ser. No. 798,032, filed Nov. 14, 1985, and now U.S. Pat. No. 4,758,583; which is a division of Ser. No. 590,820, filed Mar. 19, 1984, and now U.S. Pat. No. 4,665,192; and said Ser. No. 07/605,654, being a continuation-in-part of Ser. No. 264,930, filed Nov. 2, 1988, and now U.S. Pat. No. 4,983,604; which is a continuation-in-part of Ser. No. 119,958, filed Nov. 13, 1987, and now U.S. Pat. No. 4,908,446; which is a continuation-in-part of Ser. No. 798,032, filed Nov. 14, 1985, and now U.S. Pat. No. 4,758,583; which is a continuation-in-part of Ser. No. 590,820, filed Mar. 19, 1984, and now U.S. Pat. No. 4,665,192. Applicants claim the benefits of these Applications under 35 U.S.C. §120.

BACKGROUND OF THE INVENTION

1. Field of the Invention

The present invention is directed generally to the reaction that occurs between glucose and proteins, and more specifically, to the identification of a new group of compounds which form during nonenzymatic browning and whose existence became apparent by the studies of the inhibition of this reaction by aminoguanidine and its related analogs.

2. Description of the Prior Art

About eighty years ago, Louis Maillard first investigated the reaction of reducing sugars with the free amino groups of amino acids and proteins. This complicated reaction, termed the Maillard reaction, or non-enzymatic browning, is responsible for the aroma and taste in cooked or preserved foods.

This reaction is initiated by the reaction of primary amines (from amino acids, proteins and nucleic acids) with sugars to form imines (Schiff bases) which undergo a rearrangement to form Amadori products (AP) (see Scheme 1, below). Further rearrangements of the Amadori product are responsible for the browning and fluorescent products which lead to the formation of advanced glycosylation endproducts (AGEs).

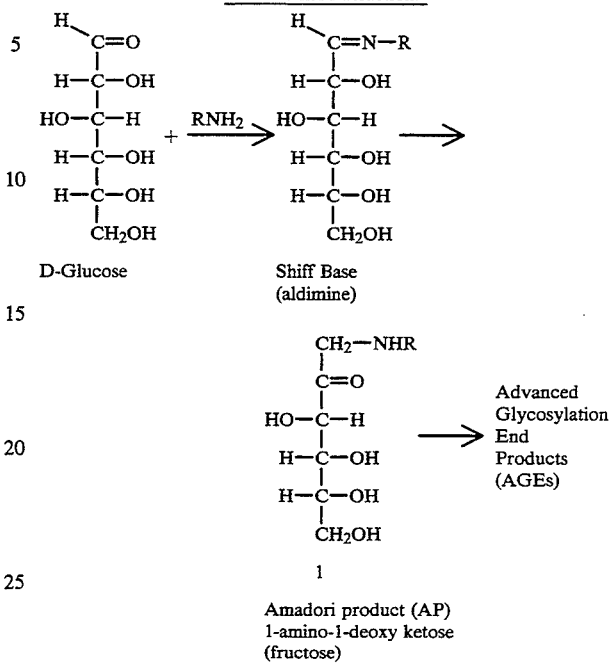

Scheme 1.
The Maillard Reaction.

Over the last fifteen years, it has been demonstrated that the Maillard reaction also occurs in vivo. A variety of proteins, such as hemoglobin, lens crystallins, connective tissue collagen, glomerular basement membrane and nerve tissue proteins, are modified by glucose in normal individuals. In diabetic patients the level of Amadori product is generally 2–3 fold higher than non-diabetics. Thus, the advanced glycosylation endproducts from Amadori product play an important role in the pathogenesis of the complications in diabetes and aging.

The chemistry of AGE formation is not yet well understood because of its extreme complexity. A variety of Maillard compounds have been identified from incubations prepared at high temperature or under acidic conditions. There is little structural information about Maillard compounds which form under physiological conditions. In 1986, Brownlee et al. found aminoguanidine to be an effective inhibitor of advanced glycosylation. Later it was shown that aminoguanidine-treated diabetic animals had significantly less collagen-linked fluorescence and crosslinking in the vascular wall than the untreated ones. Presently, aminoguanidine has displayed excellent efficacy in treating a variety of diabetic complications and is undergoing clinical efficacy trials.

The precise mechanism by which aminoguanidine and its analogs prevent advanced glycosylation is unknown. Several deoxydiketoses are detected as the degradation products of the Amadori products at various pHs and at elevated temperature, for example, 1-deoxyglucosone, 3-deoxyglucosone and 4-deoxyglucosone (see Scheme 2 below). In most studies to date, these compounds have been obtained under non-physiological conditions (high concentrations, low pH and high temperature). For example, 3-deoxyglucosone was formed preferably under acidic conditions. Furthermore, these compounds are very unstable and proof of their existence is often via chemical derivatization.

Scheme 2.
Deoxydiketoses are the degradation products of Amadori product.

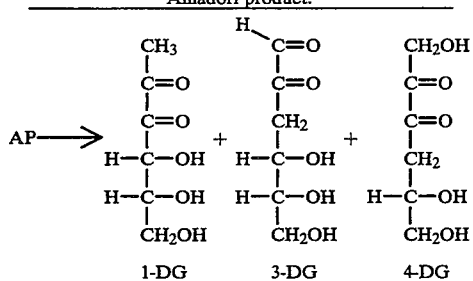

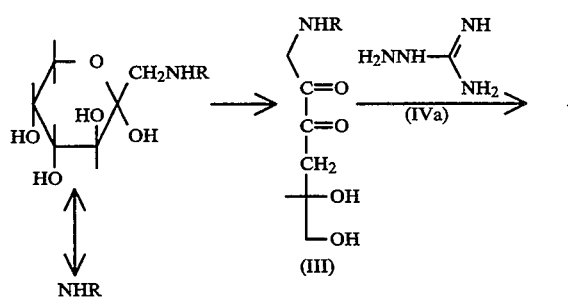

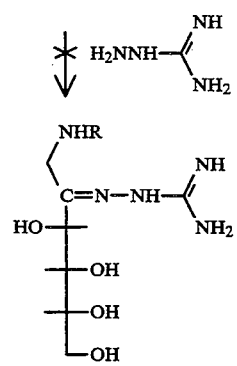

alkyl-1,2,4-triazine, results from the reaction of the rearrangement product, 1-propylamino-1,4-dideoxyosone of formula (III) with one molecule of aminoguanidine of the formula

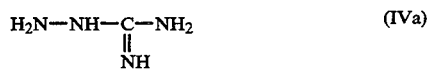

(IVa)

as shown below in Scheme 3. The second, the dihydrazone of 1,4-dideoxyglucosone (see below Scheme III) of formula (IIa), involves the further reaction with a second molecule of aminoguanidine.

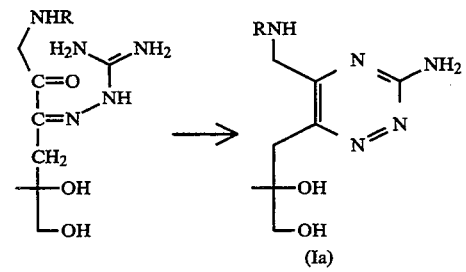

(Ia)

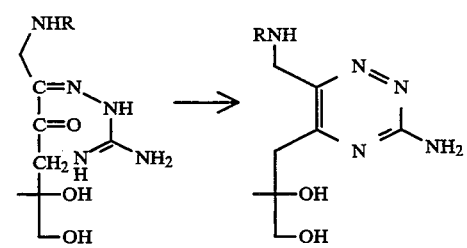

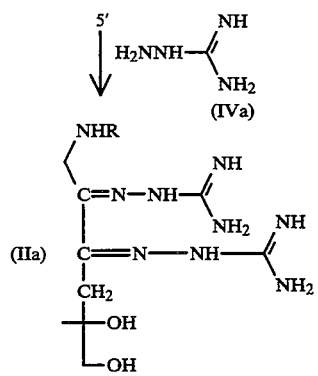

(IIa)

SUMMARY OF THE INVENTION

In accordance with the present invention, compounds of formulae I and II have been isolated and identified which are found to be present in aminoguanidine-inhibited Maillard reactions inhibited by aminoguanidine or its analogs. The first of these compounds of formula Ia, 3-amino-5-alkylaminomethyl-6-

Correspondingly, the present invention relates to the synthesis of these novel compounds by the nonenzymatic browning reaction of the named proteins with reducing sugars in the presence of aminoguanidine, or one of its analogs.

The analogs of aminoguanidine which similarly react with 1-alkylamino-1,4-dideoxyosone of formula III

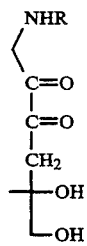

(III)

wherein R is a lower alkyl group of 1 to 6 carbon atoms, are those of the formula

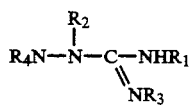

(IVb)

wherein $R_1$ is hydrogen or a lower alkyl group of 1-6 carbon atoms, amino, or hydroxy, or together with $R_2$ represent a lower alkylene bridge of 2-4 carbon atoms; $R_2$ is hydrogen, or a lower alkyl group of 1-6 carbon atoms, a hydroxyethyl group or $R_2$ may be taken together with $R_1$ as noted above; $R_3$ is hydrogen, a lower alkyl group of 1-6 carbon atoms or may be together with $R_1$ a lower alkylene bridge of 2-4 carbon atoms; and $R_4$ is hydrogen, a lower alkyl group of 1-6 carbon atoms or together with $R_3$ is a lower alkylene bridge of 2-4 carbon atoms; and their pharmaceutically acceptable salts. These compounds, their use and preparation, are disclosed in U.S. Pat. Nos. 4,758,583; 4,908,446; and 4,983,604. Thus, the reaction of the 1-propylamino-1,4-dideoxyosone III with compounds of formula IVa or IVb results in the production of compounds of the formula

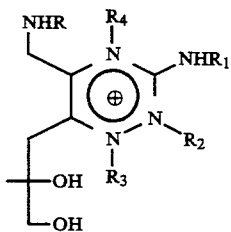

(Ib)

wherein R is a lower alkyl group of 1-6 carbon atoms and $R_1$, $R_2$, $R_3$ and $R_4$ are as hereinabove defined.

Further reaction of a compound of formula IVa or IVb with a second molecule of the compound of formula Ib will produce the corresponding compound of formula IIb

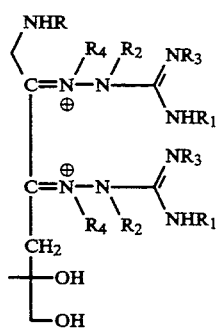

(IIb)

wherein R, $R_1$, $R_2$, $R_3$ and $R_4$ are as hereinabove defined.

The lower alkyl groups referred to above contain 1 to 6 carbon atoms and include methyl, ethyl, propyl, butyl, pentyl, hexyl, and the corresponding branched chain isomers thereof.

The rearrangement compound of formula III wherein R is a lower alkyl group is useful as a starting material for the instant preparation with the AGE-inhibitory compounds of formula IV. Additionally, it can be utilized to prepare and generate AGEs under physiological conditions where such inhibitory compounds are not present. These AGEs so prepared have utility as sunscreen agents, as well as other topical and dermal application. For example, AGEs can be incorporated into sutures to promote wound healing and minimize or prevent scar formation from surgery, etc.

The present invention also relates to a method for measuring the presence of these compounds of formulae I and II, and thus to a method for the quantitation of nonenzymatic browning in a protein material in the presence of aminoguanidine or one of its analogs. Quantitation in proteins may also indicate whether the protein had been previously exposed to aminoguanidine or one of its analogs, for example, during processing. More particularly, the presence of the compounds of formulae I and II may be followed directly by the assay techniques discussed later on, through the use of an appropriately labeled quantity of the compound. Alternately, either of the compounds of formulae I and II can be used to raise binding partners of antibodies that could, in turn, be labeled and introduced into a medium containing a protein under investigation to measure the quantity or location of the compound present in the protein sample.

Thus, both the compounds of formulae I and II of the present invention and any antibodies that may be raised therefrom, are capable of use in connection with various diagnostic techniques, including immunoassays, such as a radioimmunoassay.

In an immunoassay, a control quantity of the compound of formulae I or II, its antibody, or the like may be prepared and labeled with an enzyme, a specific binding partner and/or a radioactive element, and may then be introduced into a sample of protein material. After the labeled compound of formulae I or II or its binding partner(s) has had an opportunity to react with available protein material, the resulting mass may be examined by known detecting techniques, which may vary with the nature of the label attached.

In the instance where a radioactive label, such as the isotopes $^{14}C$, $^{131}H$, $^{125}I$ and $^{35}S$ are used, known currently available radionuclide detection procedures may be utilized. In the instance where the label is an enzyme, detection may be accomplished by any of the presently utilized colorimetric, spectrophotometric, fluorospectrophotometric or gasometric techniques known in the art.

The present invention includes an assay system which may be prepared in the form of a test kit for the quantitative analysis of the presence of nonenzymatic protein glycosylation products. The system or test kit may comprise a labeled component prepared by one of the radioactive and/or enzymatic techniques discussed herein, coupling a component of one of the advanced glycosylation endproducts, such as the present compound of formulae I or II; and one or more additional immunochemical reagents, at least one of which is a free or immobilized ligand, capable either of binding with the labeled component, its binding partner, one of the components to be determined or their binding partner(s).

In conjunction with the investigative methods and materials identified herein, the invention may extend to potential methods of treatment to either retard or inhibit the glycosylation of proteins, by a procedure involving the examination of the protein sample for the presence of the compounds of formulae I or II, in accordance with one of the methods specified earlier; followed by the development of a first binding partner or antibody to the compound of formulae I or II, the subsequent development of a second binding partner or antibody specific to the first binding partner, and the administration of the latter binding partner either to the remainder of the protein mass in the instance of foodstuffs, or the area from which the protein sample was taken in the instance of living animal tissue or serum, in an effort to prevent the protein mass from entering a further stage of the Maillard process.

It is also contemplated that the compounds of formulae I and II may be used to stimulate the immune response of an animal. Macrophages have receptors for advanced glycosylation endproducts (AGEs) which enable the body to recognize and remove AGEs. The compounds of formulae I and II may be able to stimulate macrophages to increase the activity of recognition and removal. In particular, phagocytic cells such as monocytes and macrophages are treated with a compound of formulae I or II which causes the phagocytic cells to increase their activity of recognizing and removing macromolecules such as target proteins. Detailed methodology regarding such administration is as described in U.S. Pat. No. 4,900,747, issued Feb. 13, 1990 and entitled "Method and Agents for Removing Advanced Glycosylation Endproducts." Additionally, the compounds of formulae I and II may be utilized as immune adjuvants for poorly immunogenic antigens.

The identification of the compounds of formulae I and II of the present invention makes possible the continued investigation of the Maillard process and promotes efforts to identify other specific endproducts of advanced protein glycosylation. The compounds of formulae I and II and the various investigative methods associated with its isolation and identification will associated with its isolation and identification will assist in elucidating the details of the chemical reactions that constitute late stage glycosylation, and will hopefully hold the key to identifying other specific agents that can serve to retard or inhibit the Maillard process and thereby extend the useful life of the protein. This development is particularly important as the proteins most acutely affected by the Maillard process, such as collagen, are present in substantial quantities in many important body tissues, and correspondingly exert a pronounced effect on the functioning of the body with the onset of advanced age. The condition of diabetes mellitus, with increased blood levels of glucose, would be expected to have an even more deleterious effect by promoting the formation of Maillard products in the body.

Accordingly, it is a principal object of the present invention to identify the specific compounds of formulae I and II present in protein having undergone advanced nonenzymatic glycosylation in the presence of aminoguanidine or its analogs.

It is a further object of the present invention to provide procedures for the isolation and identification of the compounds of formulae I and II as aforesaid on both an in vivo and in vitro basis.

It is a still further object of the present invention to provide methods for measurement of the compounds of formulae I and II as aforesaid which served to elucidate the stage of glycosylation of the protein sample under in investigation.

It is a still further object of the present invention to provide methods for identifying other advanced glycosylation end products in protein samples subjected to late-stage glycosylation by assay procedures utilizing the compounds of formulae I and II identified herein.

It is a still further object of the present invention to provide methods for the measurement of the current or former presence of aminoguanidine or one of its analogs in a given protein sample.

A still further object of the present invention is to measure antibodies to these compounds of formulae I or II in the body as a measure of allergy to aminoguanidine or one of its analogs.

Other objects and advantages will become apparent to those skilled in the art from a review of the ensuing description which proceeds with reference to the following illustrative drawings.

DETAILED DESCRIPTION OF THE INVENTION

In its primary aspect, the present invention concerns the isolation and identification of compounds which have been found to be present in proteins that have been incubated with a reducing sugar in the presence of aminoguanidine. In particular, such proteins exhibit several physicochemical changes, including crosslinking. The compounds which have been isolated and identified herein as formulae I and II appear to represent intermediates believed to be involved in the Maillard process which are trapped by reaction in the presence of aminoguanidine, or one of its analogs.

In order to minimize the side-products which form during the formation of the Amadori product from high concentrations of sugar, a chemically synthesized Amadori product was incubated with aminoguanidine under physiological concentration, pH, and temperature.

The Amadori product, 1-propylamine-1-deoxyfructose (1 of Scheme 3, $R = ^nPr$), was synthesized via the substitution of C1—OH of glucose with propylamine to glycosylamine, followed by rearrangement catalyzed by oxalic acid. A white powder was obtained as an oxalate after recrystallization (dioxane/methanol).

A solution of 1-propylamine-1-deoxyfructose (100 mM) and aminoguanidine (100 mM) in sodium phosphate buffer (200 mm, pH 7.4) incubated in the dark at 37° C. for 34 days had an absorption maximum at 315 nm. In the absence of aminoguanidine, the incubated Amadori product showed an absorption maximum at 290 nm with a shoulder at 340 nm. Each reaction mixture was subjected to cation exchange chromatography and eluted with a salt gradient (0 to 1M $NH_4OAc$). Fractions were collected according to the profile recorded by UV absorption at 280 nm. Three major product peaks, namely $P_1$, $P_2$, and $P_3$ were observed in the reaction mixture of the Amadori product 1 and aminoguanidine which were absent from the reaction mixture of 1 alone. The isolation of these products was difficult due to their low yields because they are transient reactive intermediates. Attempt to isolate the intermediates by silica gel chromatography failed due to decomposition. The starting material Amadori product was the major component in the incubated solution and was separated from the products by cation exchange chromatography. The products were further purified by reverse phase preparative TLC.

It is possible that aminoguanidine reacted with Amadori product 1 to form a hydrazone 2 which underwent further rearrangement to form the products (see Scheme 3). Accordingly, the hydrazone was synthesized under mild conditions: Amadori product 1 and one equivalent of aminoguanidine hydrochloride were dissolved in 90% formic acid with stirring at room temperature overnight. In the FPLC system described above, this hydrazone 2 eluted similarly to $P_2$, but $P_2$ and 2 have distinct spectral properties (UV-visible and NMR) and molecular weights (determined by FAB-MS). Also, prolonged incubation of this hydrazone did not generate products which co-eluted with $P_1$ and $P_3$. It thus appeared that aminoguanidine reacted with a previously unanticipated rearrangement product, characterized as 1-propylamino-1,4-dideoxyosone of formulae Ia. Aminoguanidine contains one imidino group and one hydrazino group which are both reactive toward carbonyl groups, the latter being more reactive than the former.

The absence of peaks in the aromatic region of the $^1$H-NMR spectrum ruled out the possibility of pyrrole or furan formation. It is proposed that the reactive intermediate 1-propylamino-1,4-dideoxyosone reacts with the hydrazine moiety of one molecule of aminoguanidine to form the monohydrazone which undergoes further dehydration/ring-closure reaction to form a stable 6-membered aromatic compound $P_1$, a 1,2,4-triazine. The ring closure reaction must be a rapid process, since no detection of this monohydrazone was observed.

There are two possible structures of the proposed 1,2,4-triazine, due to the different-reactivities of the two carbonyl groups in 3. If monohydrazone-5'-formed at the C-2 position, followed by dehydration at C-3, 3-amino-5-alkyl-6-alkylaminomethyl-1,2,4-triazine 5 would be the product. On the other hand, if monohydrazone 4' formed at C-3 with subsequent ring closure at C-2, 3-amino-5-alkylaminomethyl-6-alkyl-1,2,4-triazine 4 would be the product. Therefore, it was the reactivity of the C-2 vs. C-3 carbonyl group in which determined the structure of the product $P_1$. The former can tautomerize to its enol form at C-1 and conjugate with the nitrogen lone-pair electrons. Also, the 5-membered intramolecular hydrogen-bonding between the C-2 oxygen and the nitrogen-H might contribute to the stabilization of the C-2 carbonyl group, i.e. the C-2 carbonyl group is less reactive than the C-3 carbonyl. When Hirsh et al. reacted 3-deoxyglucosone with aminoguanidine, a mixture of the triazine isomers of a ratio of 2:1 was observed. This indicated that C-3 carbonyl is about twice as reactive as C2 carbonyl in the case of 3-deoxyglucosone. Based on the spectroscopic data ($^1$H-NMR) and FPLC trace, we did not observe any distinction of the two isomers. They must be difficult to distinguish if they both exist. The 3-amino-5-alkylaminomethyl-6-alkyl-1,2,4-triazine 4 is tentatively assigned to be the structure of $P_1$.

From NMR ($^1$H-) and Mass (FAB) spectral data, $P_3$ was proposed to be the dihydrazone 6 of 1,4-dideoxyglucosone with two molecules of aminoguanidine. This is also consistent with the fact that $P_3$ was eluted after $P_1$ on the cation exchange column. Dihydrazones of aminoguanidine with dicarbonyl sugars have been reported previously.

The reactive intermediate responsible for the formation of triazine and dihydrazone is believed to be 1-propylamino-1,4-dideoxyglucosone 3. It can be detected by Mass (FAB) spectroscopy (M.W.=203) from the early fractions of the cation exchange chromatography from incubated solutions of the Amadori product 1 both with and without aminoguanidine. Direct isolation of this reactive species on a silica gel column led to decomposition. Acetylation of the fractions containing 3 followed by silica gel chromatography provided the acetylated and dehydrated derivative 7 (see Scheme 4 below). Recently, 7 was isolated and characterized from the acetylated reaction mixture of heated Amadori product by Estendorfer et al.

Scheme 4.
7 is the acetylated product of 3

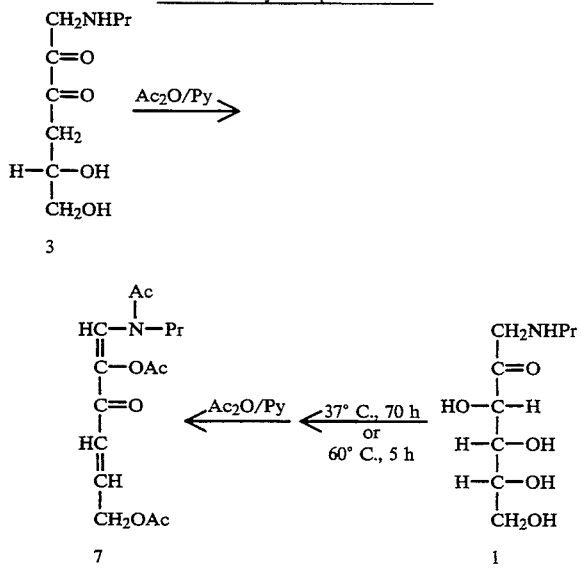

All the spectroscopic data ($^1$H- and $^{13}$C-NMR, MS (FAB, CI, EI), IR, and UV) strongly support the correct structure of 3. The trapped product with o-phenylenediamine was also reported.

Incubation of the early fractions after FPLC with aminoguanidine for short period of time (7 days) showed the production of $P_1$, $P_2$, $P_3$, on the FPLC system described above.

From the above evidence, it is apparent that the Amadori product 1 rearranges to 1,4-dideoxyglucosone 3 upon incubation under physiological pH concentration, and temperature. One or two molecules of aminoguanidine react with this intermediate to form 3-amino-5-alkylaminomethyl-6-alkyl-1,2,4-triazine or the dihydrazone of 1,4-dideoxyglucose, respectively, thus preventing further advanced glycosylation.

In general, the reactions herein represent the products of reactions of aminoguanidine or its analogs and Amadori products.

The compounds of formulae I and II the invention may be used in a variety of investigative methods, in an effort to measure the extent of nonenzymatic glycosylation of a protein sample, as well as whether aminoguanidine of analogs are or were present during the glycosylation processes. Both quantitative and qualitative determinations may be made, including the preparation of the compounds of formulae I and II with various radioactive or enzymatic labels and the introduction of the thus labeled compounds onto a protein mass to determine its state of glycosylation and chemical activity.

The compounds of formulae I and II may be labeled by a variety of techniques, depending upon the nature of the investigative procedure that is to be used. Thus, for example, the compounds of formulae I and II may be prepared with a radioactive label on the R substituent of the compound by methods known in the art.

Additionally, the labeled compound of formulae I or II can be obtained by utilizing labeled reactants in the process for producing the compounds. Other labels commonly employed for such assay procedures may also be associated with the present compound of formulae I and II and, for example, radioactive labels such as $^{14}C$ $^{131}I$, $^{3}H$, $^{125}I$, and $^{35}S$ may be appropriately introduced to the compound of formulae I or II, or to the carriers to which the compound of formulae I and II is attached.

Other known labels comprise enzymes and fluorescent materials. Fluorescent materials are preferably considered in the instance where other non-fluorescent advanced glycosylation end products are isolated and are to be labeled for use in assay systems. Similarly, fluorescent labels may be used in the instance where the compounds of formulae I and II have been employed to raise antibodies itself, which antibodies are non-fluorescent.

A number of fluorescent materials are known and can be utilized as labels. These include, for example, fluorescein, rhodamine and auramine. A particular labeled conjugate that may be developed in accordance herewith is anti-rabbit antibody prepared in goats and conjugated with fluorescein through an isothiocyanate.

Enzyme labels are likewise useful, and can be detected by any of the presently utilized colorimetric, spectrophotometric, fluorospectrophotometric or gasometric techniques. The enzyme is conjugated to the selected compounds of formulae I or II by reaction with bridging or activating molecules such as carbodiimides, diisocyanates, glutaraldehyde and the like. Many enzymes which can be used in these procedures are known and can be utilized. The preferred are peroxidase, $\beta$-glucuronidase, $\beta$-D-glucosidase, $\beta$-D-galactosidase, urease, glucose oxidase plus peroxidase and acid phosphatase. U.S. Pat. Nos. 3,654,090; 3,850,752; and 4,016,043 are referred to by way of example for their disclosure of alternate labeling material and methods.

The compounds of formulae I and II may be used to produce antibody(ies) to themselves which can be produced and isolated by standard methods including the well known hybridoma techniques. The antibody(ies) can be used in another species as through they were antigen(s) to raise antibody(ies). Both types of antibody(ies) can be used to determine the amount and location of the compounds of formulae I and II in protein masses, whether in foodstuffs, or in the mammalian body. For convenience, the antibody(ies) to the compounds of formulae I and II will be referred to herein as $Ab_1$ and antibody(ies) raised in another species as $Ab_2$.

The degree of glycosylation in protein masses suspected of undergoing the same can be ascertained by the usual immunological procedures applicable to such determinations. A number of useful procedures are known. Three such procedures which are especially useful utilize either the compound of formulae I or II labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Cp" stands for the compound of formulae I or II:

A. $Cp^* + Ab_1 = Cp^*Ab_1$
B. $Cp + Ab_1^* = CpAb_1^*$
C. $Cp + Ab_1 + Ab_2^* = CpAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" Procedure, is described in U.S. Pat. Nos. RE 31,006 and 4,016,043. Still other procedures are known such as the "Double antibody" or "DASP" procedure.

In each instance, the compound of formulae I or II substance forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using $Ab_1$ as an antigen. $Ab_2$ therefore would be anti-rabbit antibody raised in goats. For purposes of this description and claims, $Ab_1$ will be referred to as an antibody reactive with a compound antibody or, in the alternative, and "anti-antibody".

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The compound of formulae I or II or its binding partner(s) can also be labeled with a radioactive element or with an enzyme. The radioactive label can be detected by any of the currently available counting procedures. The preferred isotope may be selected from $^{14}C$, $^{131}I$, $^{3}H$, $^{125}I$ and $^{35}S$.

In a further embodiment of this invention, commercial test kits suitable for use either by a medical specialist or a food technologist may be prepared to determine the presence or absence of glycosylation end products in a suspected protein sample treated with aminoguanidine or one of its analogs. In accordance with the testing techniques discussed above, one class of such kits will contain at least the labeled compound of formulae I or II or its binding partner, and antibody specific thereto. Another which contain at least $Ab_1$ together with labeled $Ab_2$. Still another will contain at least $Ab_1$ and directions, of course, depending upon the method selected, e.g., "competitive", "sandwich", "DASP" and the , , like. The kits may also contain peripheral reagents such as buffers, stabilizers, etc.

Accordingly, a test kit may be prepared for the demonstration of these compounds in protein masses, whether in food or in animals, comprising:

(a) a predetermined amount of at least one labeled immunochemically reactive component obtained by the direct or indirect attachment of glycosylation product, the present compound of formulae I or II or a specific binding partner to either, to a detectable label;

(b) other reagents; and (c) directions for use of said kit.

More specifically, the diagnostic test kit may comprise:

(a) a known amount of the compound of formulae I or II or the glycosylation product as described above (or a binding partner) generally bound to a solid phase to form a immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

a. a labeled component which has been obtained by coupling a compound of formulae I or II to a detectable label;

b. one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the advanced glycosylation end product and a specific binding partner thereto.

By example, a solid phase assay system or kit may comprise the solid substrate with either bound binding partner and labeled compound of formulae I or II or bound compound of formulae I or II and labeled binding partner. A supernatant containing the protein to be assayed is then placed in contact with the substrate and a competitive reaction between the labeled material and any unlabeled binding partner(s) in the sample will cause the release of a quantity of the former into the supernatant whereupon it can be precisely quantitatively identified. The foregoing explanation of a particular competitive assay system is presented herein for purposes of illustration only, in fulfillment of the duty to present an enabling disclosure of the invention. It is to be understood that the present invention contemplates a variety of diagnostic protocols within its spirit and scope.

As discussed earlier, the present invention includes potential methods for treating proteins undergoing glycosylation in an effort to retard if not totally inhibit the progress of the Maillard process. The method comprises the development of anti-antibody to the compound or to other isolated glycosylation products, that when administered to the glycosylating protein mass, serves by its structure and reactivity, to block rather than facilitate the continued glycosylation of the protein.

For example, an anti-antibody or second binding partner to a first binding partner to a compound of formulae I or II might be raised as in the practice of one earlier described assay procedures, which does not cause the proteins to crosslink. In this way, the administration of this non-crosslinking binding partner may form an immune complex activating the animal's clearance system to remove said immune complex and associated AGES so that it can later be replaced. The foregoing scenario is naturally illustrative of a course of action that suggests itself as an outgrowth of the findings as to the aging process disclosed presently herein. Additionally, the compounds of formulae I or II of this invention can be utilized as adjuvants due to their cross-linking potential with antigens and also as macrophage stimulants to activate the macrophage to effect removal of AGEs. When a compound of formulae I or II is utilized as an adjuvant it is reacted or cross-linked with an antigen that is "weak". The addition of compound of formulae I or II to the antigen produces an antigen which produces a strong reaction due to the presence of the compound portion, thus increasing the immunogenicity of the original antigen. The invention is not limited to this methodology, but rather encompasses it within its scope. As noted earlier, phagocytic cells are capable of recognizing and removing abnormal macromolecules by means of receptors on their surfaces which recognize specific chemical structures and bind them. Once the abnormal macromolecule is recognized in this way, the phagocytic cell may internalize the macromolecule and may then degrade it. In some instances, the phagocytic cell may in addition secrete enzymes and other factors to help degrade it. In some instances, the phagocytic cell may in addition secrete enzymes and other factors to help degrade the molecule or particle extracellularly if it cannot be internalized. After the damaged protein is removed, new growth of normal tissue can ensue, and normal function of the affected area may resume.

Phagocytic cells in the body comprise numerous types of white blood cells. One type of white blood cell, the monocyte, is produced in the bone marrow, and circulates briefly in the blood and thereafter enters the tissues where it becomes a macrophage.

Thus, the present invention is predicted on the discovery that the phagocytic cells including monocytes and macrophages can be modified by exposure to stimulator compounds that potentiate the capability of these cells with respect to their recognition and affinity for, and capability to degrade advanced glycosylation end products. In particular, the exposure of these cells to certain stimulator compounds has been found to increase the number of receptors developed on these cells and to thereby increase the capacity and efficiency of these cells with respect to the recognition and degradation of advanced glycosylation endproducts. The compounds of formulae I and II of the present invention can function as stimulator compounds.

Accordingly, the method of the present invention generally comprises exposing the animal body to stimulator compounds of formulae I or II, which cause the body, an its phagocytic cells in particular to become activated and to increase its recognition and removal of target macromolecules that have undergone advanced glycosylation.

The stimulator compounds useful in the present invention comprise the triazine or dihydrazone compounds of formula I or II which may be employed alone or bound to a carrier.

The stimulator compounds can be bound to a carrier protein such as the protein albumin.

The carrier may be selected from the group consisting of carbohydrates, proteins, synthetic polypeptides, lipids, bio-compatible natural and synthetic resins, antigens and mixtures thereof.

As used herein, the term "antigen" includes various invasive stimuli that may comprise or cause the onset of pathology or other organic disability, such as protein and lipid fragments, bacteria, viruses and/or other organisms of similar origin and effect.

An additional and related utility of the compounds involves their usage to detect the presence of the aminoguanidine allergy in humans. This can be accomplished by testing the serum of a patient for the presence of antibodies to either the triazine or dihydrazone compounds. Since an allergic reaction may be the result of sensitization of an individual to derivatives of formulae I and II formed in the presence of aminoguanidine, the characteristic antibodies will be present in the allergic individual's serum.

As mentioned earlier, the isolation and identification of the compounds of formulae I and II of the present invention involved the performance of a series of procedures upon representative proteins. The specific procedures and materials that were used in the preparation of the proteins, and the isolation and analysis of the compounds that followed, are set forth below in the following illustrative examples.

EXAMPLE 1

General methods $^1$H- and $^{13}$C-NMR spectra (chemical shifts in parts per million from the internal tetramethylsilane) were recorded either on a General Electric QE-300 or a Brucker AM 360 WB spectrometer. UV visible spectra were measured on either a Hewlett-Packard 8450A or 8452A diode array spectrophotometer. Fast atom bombardment (FAB) mass spectra were performed using a VG 707E double focussing mass spectrometer and run from a glycerol/0.1% acetic acid matrix. Chemical ionization (CI) mass spectra were obtained on a Hewlett-Packard model 5988A spectrometer. High resolution electron impact (EI) mass spectra were obtained on a VG-II-250 spectrometer. FT-IR spectra were performed on a Mattson model Polaris instrument.

Silica Gel 60 $F_{254}$ (Analtech 59527) and reverse phase $C_{18}$ (Analtech 52011 & 63527) were used for TLC and Silica Gel 60 (Fluka 60738) for column chromatography. All chemicals were reagent grade or better. Fast protein liquid chromatography, were performed using a Pharmacia Mono S HR 16/10 column.

1-Propylamino-1-deoxy-D-fructose oxalate (1).

The synthesis was performed essentially according to the method described by F. Micheel and G. Hagemann. White crystals were obtained in 65% total yield from and-glucose $^1$H-NMR (D$_2$O) (δ0.91 (t, J=7.5 Hz, 3H), 1.66 (sext., J=7.5 Hz, 2H), 3.01 (t, J=7.5 Hz, 2H), 3.24 (s, 1H), 3.71 (m, 2!i), 3.83 (dd, J=9.6, 3.6 Hz, 1H), 3.97 (m, 2H); Mass spectrum (Xe(+)-FAB): 222.

EXAMPLE 2

Isolation of 3-Amino-5-propylaminomethyl-6-(2', 3',dihydroxypropyl)-1,2,4-triazine (4) and 1-Propylamino-2,3-diaminoguanidine-1,4-dideoxyglucosone Dihydrazone (6)

A solution containing 1 (100 mM), aminoguanidine (100 mill) and sodium phosphate (200 mM, pH 7.4) was incubated at 37° C. for 34 days. The solution was then chromatographed on a Pharmacia FPLC (Mono S. HR 16/10) with flow rate of 3 ml/min and eluted 10 min with B40, 40 min with a gradient from 0 to 1M NH$_4$OAc and 15 min with 1M NH$_4$OAc. Each fraction was collected for one minute@ Fractions from 52–60 min were combined and lyophilized. The mixture was separated on a preparative reverse phase t.l.c. with MEOH/1M NH,OAC (4/1). 4: $^1$H-NMR (D$_2$O) δ0.93 (t, J=7.5 Hz, 3H), 1.67 (sext., J=7.5 Hz, 2H), 3.02 (t, J=7.5 Hz, 2H), 3.18 (s, 1H), 3.5–4.3 (m, SH)t 8.SO (S, 1H); Mass spectrum (Xe(+)-FAB): 242; UV(H20)..: 315 nm. 6: $^1$H-NMR (D$_2$O) δ0.95 (t, J=7.5 Hz, 3H), 1.69 (sext, J=7.5 Hz, 2H), 3.04 (m. 4H), 3.36 (dd, j=12.9, 2.7 z, 1H), 3.85 (m, 2H), 7.74 (s, 1H); Mass spectrum (Xe(+)-FAB): 316; UV (H$_2$O)$_{max}$: 287 nm.

EXAMPLE 3

Synthesis of 1-propylamino-1-deoxyfructose guanylhydrazone (2).

To a solution of 1 (96 mg, 0.31 mmol) in 5 ml of 90% formic acid was added aminoguanidine hydrochloride (32 mg, 0.29 mmol) with stirring at room temperature for 16 hours. The reaction mixture was evaporated and dried under reduced pressure. The monohydrazone was obtained as a brownish solid in quantitative yield. $^1$H-NMR (D20) δ1.00 (t,, J=7.5 Hz, 3H), 1.75 (sext, J=7.5 Hz, 2H), 3.10 (t,, J=7.5 Iiz,, 2Ii), 3.32 (s, 1H), 3.77 (m, 2H), 3.92 (m, 1H), 4.03 (m, 2!i), 8.26 (s, 1H); Mass spectrum (Xe(+)-FAB): 278; UV(H$_2$O)$_{2max}$: 285 nm.

Detection of 1-propylamino-1,4-dideoxy-2,3-hexodiulose (3).

Fractions collected from 6–9 min from the Mono S chromatography of the incubation mixture of 1 and aminoguanidine hydrochloride described before were lyophilized and submitted for Mass spectroscopic analysis. Mass spectrum (Xe(+)-FAB): 204.

Fractions collected from the incubated mixture of 1 (sodium phosphate, pH 7.4) alone also resulted in a value of 204 by Mass (Xe(+)-FAB) spectroscopy.

EXAMPLE 5

Isolation of acetylated aminoreductone 7.

To the dried fractions #6–9 (1.1 g including sodium phosphate) from the incubated mixture of 1 and AG-HCL was added acetic anhydride (11.7 ml) and pyridine (10.0 ml). The reaction was stirred at room temperature for 17 hours. The reaction mixture was then poured into ice and extracted with ethyl acetate (200 ml). The evaporated residue was purified by preparative SiO2 TLC with Hexane/EtOAc/Et$_3$N (50/50/1) and extracted with MeOa. $^1$H-NMR (CDCl$_3$) δ0.93 (tt J=7.5 az, 3H), 1.62 (sext, J-7.5 Hz, 2H), 2.13 (s, 3H), 2.30 (s, 3H), 2.34 (s, 3E), 3.69 (tt J % 7.5 Hz, 2H), 4.77 (dd, J=4.5, L.5 Hz, 1E), 6.67 (d, J=15.31 1H), 6.91 (dt, J=15.3@ 4.5 Hz, IH), 7.83 (br s. 1H); $^{13}$C-NMR (COC$_{13}$) 8 11.10, 20.48, 20.72t 22.03, 22.38t 47.43f 63.02, 124.112f 127.75, 130.87, 140.31t 168.43, 170.48, 183.25; Mass spectrum (Xe(+)-FAB): 312; Mass spectrum (EI): 311, 269, 227, 19 1 IL6′71 1.5,4, 3.3EI, 100,70, 43; Mass spectrum (CI): 312, 298, 270, 252, 228, 210, 186, 168, 142t 102t 85; UV (EtOH).,: 300 nm; FT-IR (KBr) 2955, 2927, 2856, 1762, 17S4t 1698, 1636, 1624t 1374f.1261t 229f 1193, 1146, 1083t 1045, 806.

What is claimed is:

1. A compound selected from the group consisting of compounds of the formula

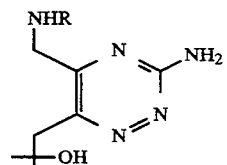

(Ia)

and

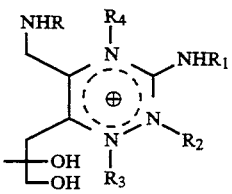

(II)

wherein R is a lower alkyl group of 1 to 6 carbon atoms;
R$_1$ is hydrogen or a lower alkyl group of 1–6 carbon atoms, amino, or hydroxy, or together with R$_2$ represent a lower alkylene bridge of 2–4 carbon atoms;
R$_2$ is hydrogen, or a lower alkyl group of 1–6 carbon atoms, a hydroxyethyl group or R$_2$ may be taken together with R$_1$ as noted above;
R$_3$ is hydrogen, a lower alkyl group of 1–6 carbon atoms or may be together with R$_1$ a lower alkylene bridge of 2–4 carbon atoms;
and R$_4$ is hydrogen, a lower alkyl group of 1–6 carbon atoms or together with R$_3$ is a lower alkylene bridge of 2–4 carbon atoms; and their pharmaceutically acceptable salts.

2. A compound according to claim 1 wherein R is lower alkyl and R$_1$, R$_2$, R$_3$ and R$_4$ are each hydrogen, and their pharmaceutically acceptable salts.

3. The compound according to claim 1 which is 3-amino-5-propylaminomethyl-6-(2′,3′-dihydroxypropyl)-1,2,4-triazine or a pharmaceutically acceptable salt thereof.

4. An indicator composition for use in an assay procedure for the detection of advanced glycosylation endproducts in polypeptide samples, said composition comprising a compound selected from the group consisting of compounds of the formula

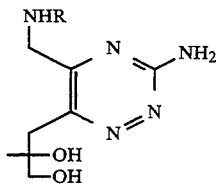

(Ia)

and

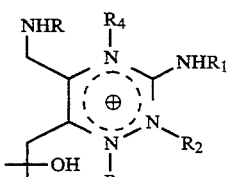

(Ib)

wherein R is a lower alkyl group of 1 to 6 carbon atoms;
R$_1$ is hydrogen or a lower alkyl group of 1–6 carbon atoms, amino, or hydroxy, or together with R$_2$ represent a lower alkylene bridge of 2–4 carbon atoms;
R$_2$ is hydrogen, or a lower alkyl group of 1–6 carbon atoms, a hydroxyethyl group or R$_2$ may be taken together with R$_1$ as noted above;
R$_3$ is hydrogen, a lower alkyl group of 1–6 carbon atoms or may be together with R$_1$ a lower alkylene bridge of 2–4 carbon atoms;
and R$_4$ is hydrogen, a lower alkyl group of 1–6 carbon atoms or together with R$_3$ is a lower alkylene bridge of 2–4 carbon atoms; and their pharmaceutically acceptable salts.

5. An indicator composition according to claim 4 for use in an assay procedure for the detection of advanced glycosylation endproducts in polypeptide samples, said composition comprising a compound which is a 3-amino-5-alkylaminomethyl- 6-alkyl-1,2,4-triazine of the formula (Ia).

6. A composition for promoting the sequestration and removal from the body of an animal of target macromolecules that have undergone advanced glycosylation comprising a compound of claim 1 capable of causing the body to increase its activity of recognizing and removing said macromolecules.

7. The composition of claim 6 wherein said compound is bound to a carrier.

* * * * *